United States Patent [19]
Trainer

[11] Patent Number: 6,104,491
[45] Date of Patent: Aug. 15, 2000

[54] SYSTEM FOR DETERMINING SMALL PARTICLE SIZE DISTRIBUTION IN HIGH PARTICLE CONCENTRATIONS

[75] Inventor: Michael N. Trainer, Telford, Pa.

[73] Assignee: Microtrac, Inc., Montgomeryville, Pa.

[21] Appl. No.: 09/211,374

[22] Filed: Dec. 14, 1998

[51] Int. Cl.[7] .................................................. G01N 15/02
[52] U.S. Cl. ............................................ 356/336; 356/246
[58] Field of Search ..................................... 356/335, 336, 356/338, 393, 246

[56] References Cited

U.S. PATENT DOCUMENTS

| | | | |
|---|---|---|---|
| 5,017,008 | 5/1991 | Akiyama | 356/336 |
| 5,094,532 | 3/1992 | Trainer et al. | 356/336 |
| 5,416,580 | 5/1995 | Trainer | 356/336 |
| 5,594,545 | 1/1997 | Saito et al. | 356/246 |
| 5,684,584 | 11/1997 | Nakamoto et al. | 356/336 |

Primary Examiner—Frank G. Font
Assistant Examiner—Layla Lauchman
Attorney, Agent, or Firm—Wood, Herron & Evans, LLP

[57] ABSTRACT

A system is disclosed for determining the distribution of the size of small particles contained in a sampled portion of a process stream containing particles at high concentrations. The system includes a light delivery arrangement that anamorphically modifies light energy received from a light source and projects the anamorphically modified light energy to an optical element contained in a sample cell. The optical element includes a passage that is arranged to receive therein particles of a predetermined size from the sampled portion of the process stream flowing in the sample cell. The anamorphically modified light energy is transmitted through the optical element and is focused within the passage to irradiate the particle ensemble therein. A light collection arrangement collects the light energy escaping from the optical element and focuses the light energy collected onto a detector array. The detector array develops output signals used to determine a measurement of the distribution of the size of the particles contained in the process stream.

8 Claims, 4 Drawing Sheets

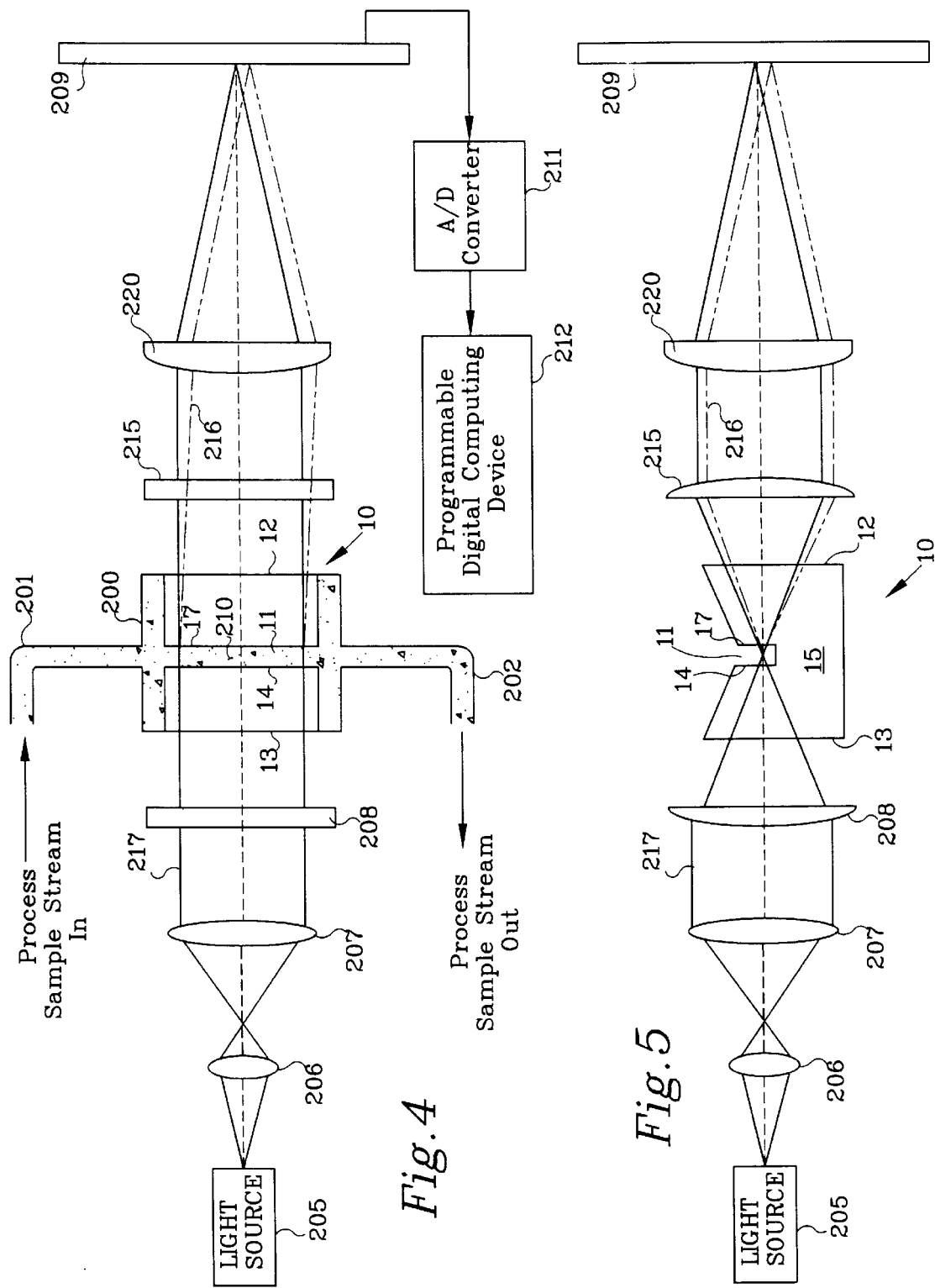

SYSTEM FOR DETERMINING SMALL PARTICLE SIZE DISTRIBUTION IN HIGH PARTICLE CONCENTRATIONS

CROSS REFERENCE TO RELATED APPLICATIONS

This present application is related to applicant's co-pending patent application Ser. No. 09/211,373, entitled "A MULTIPLE PATHLENGTH SENSOR FOR DETERMINING SMALL PARTICLE SIZE DISTRIBUTION IN HIGH PARTICLE CONCENTRATIONS", filed on an even date herewith and assigned to a common assignee with the present invention.

BACKGROUND OF THE INVENTION

1. Field of the Invention

The present invention relates generally to the field of determining particle size distribution and more specifically to a system for measuring particle size distribution using static light scattering techniques in particle dispersions or process streams having high particle concentrations.

2. Discussion of the Related Art

The measurement of particle size distribution finds use in the process industries in the manufacture of pharmaceuticals, chemicals, abrasives, ceramics, pigments and the like, where the particle size affects the quality of the manufactured product.

A number of methods presently exist for determining the size distribution of particulate material for particles in the approximate size range of 0.1 to 1000 microns in diameter. The conventional method of measurement at high concentration is dynamic light scattering, as taught by U.S. Pat. No. 5,094,532 to Trainer et al, patented Mar. 10, 1992. This patent discloses a fiber optic Doppler anemometer and method that directs a beam of light into a scattering medium that contains particles in Brownian motion. The frequency of the scattered light is compared to non-scattered light emitted from the scattering medium and results in the generation of a first signal having a magnitude that is indicative of the difference in frequency between the scattered light and the non-scattered light. A second signal is generated having a magnitude that varies with frequency on a linear scale. The frequency scale of the second signal is then translated into a logarithmic scale and deconvolved to determine the size and distribution of moving particles within the scattering medium. The translation and deconvolving requires translation of analog signals to digital signals and subsequent processing by a central processor and a vector signal processor using fast Fourier transfer techniques (FFT). In order to solve for a known particle size distribution of over 80 particle diameters the method just described must sample over 80 frequencies. Even though this method provides an accurate measurement of particle size distribution, it does require a long time period (usually greater than two minutes) to process all of the sample frequencies, due primarily to the stochastic nature of Brownian motion. This technique is best suited for use in a laboratory with samples that have been extracted from a process and properly prepared for measurement analysis. Additionally, this method is strongly dependent upon dispersant viscosity and temperature and the use of non-flowing sample delivery systems. Although this technique provides accurate results for particles having diameters less than 1 micron, it exhibits poor size and volume accuracy for particles above 1 micron.

Another recognized technique and method for measuring the size distribution of very small particles is static light scattering, or angular light scattering. In this method, a collimated monochromatic light beam irradiates an ensemble of particles that flow perpendicularly through the collimated light beam. Light scattered from the particles emerges from the interaction over a range of angles from the axis of the collimated beam. The scattered light is collected by a lens placed in the path of the scattered light. The scattered light patterns focused in the focal plane of the lens are typically measured by an array of photodetectors placed in the focal plane. The angular extent of the scatter pattern is determined by the size of the particles. The smaller the particle, the wider the angular extent of the scatter; the larger the particle, the narrower the angular extent of the scatter.

One such method is taught by U.S. Pat. No. 5,416,580 to Trainer, patented on May 16, 1998, which uses multiple light beams to irradiate the particles. This method has demonstrated excellent measurement results for particles in the 0.1 to 3000 micron range in flowing sample systems, without temperature or viscosity dependency. Unlike the dynamic scattering techniques, measurements can be made in less than five seconds with repeatability superior to that of the dynamic light scattering. However, in order to produce good measurement accuracy for a process sample at a high concentration, for example 10% by volume, the process sample must be properly diluted with a dispersant medium to minimize the particle concentration.

The particle concentration capability of static light scattering is limited primarily due to multiple scattering, where primary scattering from a particle does not reach the detector without being re-scattered by at least one other particle. This re-scattering distorts the angular scattering distribution from the ensemble of particles and changes the calculated size distribution. Therefore, presently known static light scattering methods require a sample to be extracted from the process and properly diluted by a dispersing medium for the introduction to a light scattering measurement instrument. In many processes, sample dilution will cause a change in the size distribution.

BRIEF SUMMARY OF THE INVENTION

It is, therefore, an object of the present invention to provide a system for the accurate measurement of particle size distribution using static light scattering techniques at high particle concentrations.

It is also an object of the present invention to provide a system for the accurate measurement of particle size distribution using static light scattering techniques that can be used for the online particle size measurement for process control.

In accordance to the objects, the present invention is used with an apparatus for determining the size distribution of small particles contained in a process stream. The apparatus includes a sample cell having an inlet for receiving a sample portion of the process stream and an outlet for returning the sample portion to the process stream. The apparatus further includes a light source for generating light energy, a detector array for receiving light energy and means for translating the detected light energy into a particle size distribution measurement.

The system of the present invention comprises a light delivery arrangement that anamorphically modifies the light energy received from the light source and projects the anamorphically modified light energy to the sample cell. An optical element composed of an optically clear material is contained in the sample cell. The optical element includes a passage in the form of a channel that is exposed to the sample portion of the process stream flowing in the sample cell. The passage is sized to receive particles of a predetermined size range. The anamorphically modified light energy is transmitted through the optical element and is focused substantially along the passage to irradiate the particle ensemble therein. The light energy scattered by the particle ensemble, as well as the incident light energy, are projected back into the optical element.

A light collection arrangement collects the light energy escaping from the optical element and modifies the collected light energy for projection and focus on the detector array.

Output signals representing the angular distribution of the detected scattered light are generated by the detector array and used to determine a measurement of the distribution of the size of the particles contained in the process stream.

BRIEF DESCRIPTION OF THE SEVERAL VIEWS OF THE DRAWINGS

Other objects, features, and advantages of the present invention will be apparent from the following description of a preferred embodiment thereof, taken in conjunction with the sheets of drawings, in which:

FIG. 4 depicts, in a horizontal block diagram view, the optical element of FIG. 3A, used in conjunction with the light delivery and light collection arrangement of the system of the present invention;

FIG. 5 depicts the system of the present invention shown in FIG. 4 in a block diagram form viewed in a vertical plane.

DETAILED DESCRIPTION OF THE INVENTION

Figure 1:
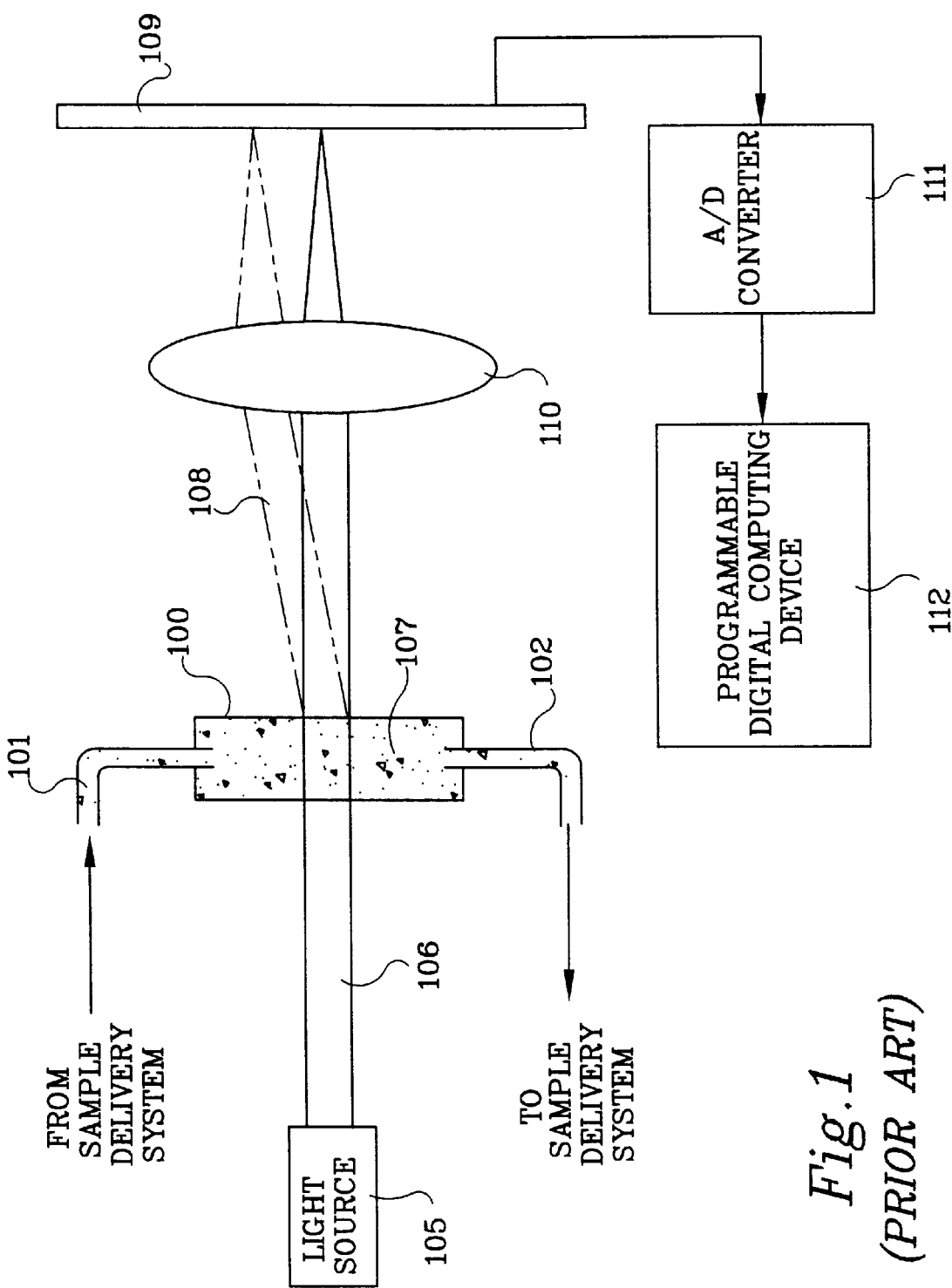
FIG. 1 illustrates, in the form of block diagram, a prior art device for determining the particle size distribution of process stream samples prepared for analysis by diluting the concentration and suspending the particles in a diluting medium.

Although well known by those skilled in the art, a brief description of a presently known apparatus used for obtaining particle size distribution by measuring the angular distribution of scattered light will be set forth in order to help understand the present invention. With reference to FIG. 1, a particle analyzer shown in block diagram operates with a sample delivery system (not shown) that delivers prepared particle samples in a sample stream to a sample cell 100. The particles being measured are typically suspended in a dispersing or diluting medium contained within the sample system. The dispersing medium acts not only as a carrier medium for the particles but also as the required diluting medium to provide the proper dilution of particle concentrations required by the prior art particle analyzer. The sample stream is continually circulated from a reservoir of the sample delivery system into an inlet conduit 101, through sample cell 100, out of cell 100 via outlet conduit 102 and back to the reservoir. The device of FIG. 1 further includes a light source 105, which generates a light beam (preferably collimated) 106 shown passing through sample cell 100, which contains the particle ensemble 107. Incident light beam 106 and scattered light beam 108 (the product of the light from beam 106 scattered by particles 107) are shown focused on detector array 109 via a single collector lens 110. The detector array 109 outputs analog signals representing the total scattered light intercepted by individual detector elements of the detector array 109. The analog detector array output signals are typically converted to digital signals by A/D conversion techniques by an A/D converter 111 and subsequently processed by a programmable computing device 112 by using well known inversion techniques to obtain the desired particle size distribution.

The static light scattering particle analyzer just described finds disadvantage in that the particle sample must be extracted from the process stream of the manufacturing process and diluted in a dispersant medium for introduction to the particle analyzer. In many processes, particle sample dilution will cause a change in the size distribution. Additionally, the apparatus used to extract the samples jeopardizes the integrity of the manufacturing process stream.

The dilution of the extracted particle samples in a static light scattering particle analyzer is required due primarily to the phenomenon of multiple scattering. That is, in samples of high particle concentration, the light initially scattered from a particle does not reach the detector without being re-scattered by at least one other particle. This re-scattering distorts the angular scattering distribution from the group of particles and changes the calculated size distribution. Multiple scattering is proportional to the product of the particle scattering cross section and the optical pathlength of the sample. Therefore, reducing the sample cell pathlength, while still allowing sufficient space for the largest particles, can reduce the effects of multiple scattering in high concentration particle samples.

The present invention discloses a system that includes an optically clear element having a channel formed thereon that is exposed to the particle stream. The channel has a short pathlength that greatly reduces the effects of multiple scattering and, therefore, increases the upper concentration limit that can be effectively used to measure particle size distribution.

Figure 2:
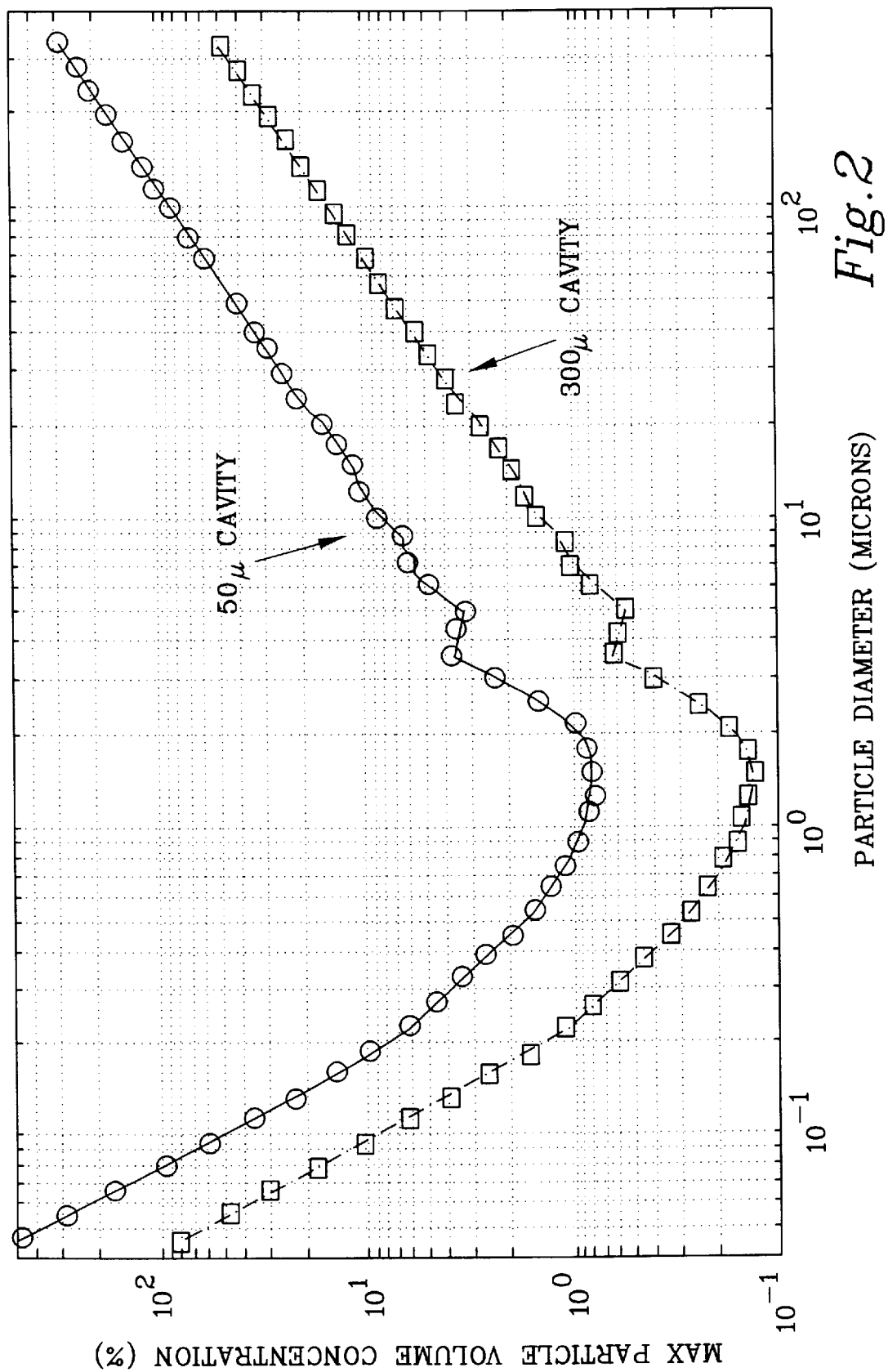
FIG. 2 illustrates, in the form of a graph plot, the theoretical upper concentration limit of two optical channels having pathlengths of 50 and 300 microns.

Turning now to FIG. 2, a graphical representation of the theoretical concentration sampling of two optical channels having pathlengths of 50 and 300 microns is shown. Using the experimental result of 64% transmission for 0.02% concentration of 1.33 micron particles as a basis, a maximum concentration curve can be generated based upon theoretical scattering cross section per unit volume. The data depicted in FIG. 2 only approximates the true concentration limits, which typically must be calculated from multiple scattering theory. However, it is a reasonable approximation for the explanation of this embodiment.

As can be seen in FIG. 2, the cross section per unit particle volume is inversely proportional to particle diameter for particles above 2 microns in size. In the 50 micron curve a worst case volume concentration limit is shown as 1% at a particle diameter of 1.2 microns, increasing to 10% at 0.2 and 10 microns. The 300 micron channel curve exhibits a scattering cross section per unit volume that decreases for larger particle diameters, allowing for greater than 10% concentration at the 300 micron pathlength for the larger particles.

It will be appreciated by those skilled in the art that the choice of 50 and 300 micron channels is for example only. The actual optimum channel size will depend on the particle size range and the concentration of the particles in the sampled process stream.

Figure 3B:
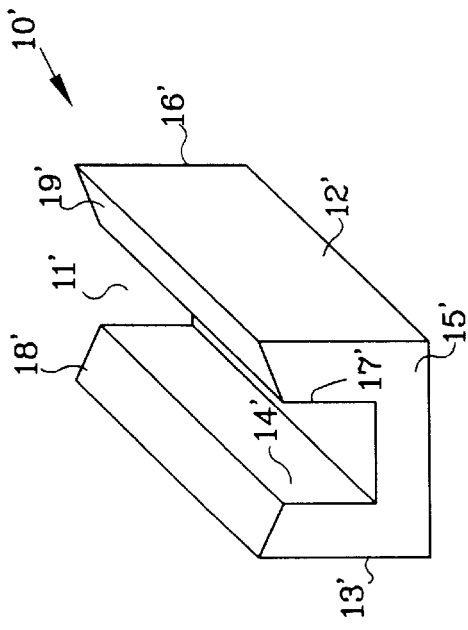
FIG. 3B depicts the optical element having a 300 micron channel formed thereon in accordance to the present invention.
Figure 3A:
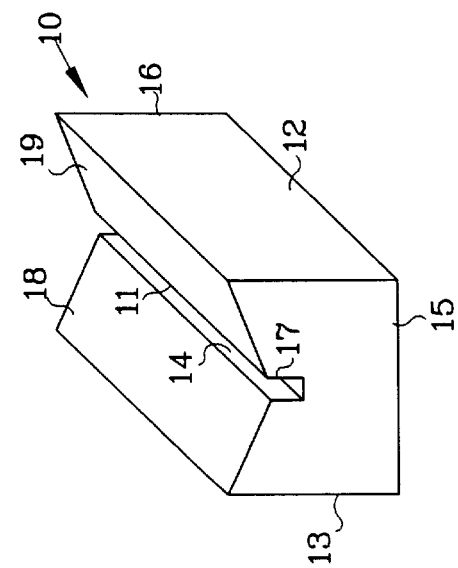
FIG. 3A depicts an optical element having a 50 micron channel formed thereon in accordance to the present invention.

FIG. 3A shows the optical element 10 of the present invention having a 50 micron channel 11 formed thereon. Optical element 10 is generally a rectangular structure that includes vertical sidewalls 12 and 13 extending between a pair of end walls 15 and 16. A 50 micron wide channel 11 is centrally located between a pair of top surfaces 18 and 19, with the channel 11 extending longitudinally from end wall 15 to end wall 16. Top surfaces 18 and 19 extend upward obliquely from channel 11 to associated sidewalls 13 and 12 respectively. The optical element is composed of an optically clear material, such as fused silica or the like. The depth of channel 11 is approximately equal to the pathlength (or width of channel 11) to provide a shallow channel, which allows easy exchange of particles with the sampling stream.

FIG. 3B shows the optical element 10' of the present invention exhibiting a 300 micron channel 11' formed thereon. Optical element 10' has the same structure as optical element 10, having, however, a channel 11' that is 300 microns wide. As in the case of channel 11, channel 11' has a depth that is approximately equal to the pathlength (or width of channel 11') to provide a channel which allows easy exchange of particles with the sampling stream. Each of the optical elements 10 and 10' is arranged to be installed within the sampling cell with the sample particle stream flowing through and over channels 11, 11'.

Turning now to FIG. 4, the system of the present invention is illustrated using the 50 micron optical element installed in a sample cell 200. Sample cell 200 receives particle samples in the form of a sample stream from an inlet tube 201. The sample stream received flows through sample cell 200 with a portion of the particle samples flowing within channel 11. The sample stream exits the sample cell 200 via outlet tube 202. The inlet tube 201 and outlet tube 202 can be connected to a sample delivery system as described above in the particle analyzer of FIG. 1, or alternatively, can be connected to a bypass line from the manufacturing process stream. The bypass line would deliver directly to the system of the present invention, a portion of the manufactured process stream and the particles contained therein for analysis.

The present invention further includes a light delivery and light collection arrangement that includes a source of light energy 205. Either a laser or laser diode can be effectively used as the light source 205. The light energy radiated by light source 205 is received by a first projection lens 206 that broadly focuses the beam of light from light source 205 onto a collimator lens 207. The collimated light from lens 207 is next applied to a first cylindrical lens 208. Since the light scattered by sample particles 210 must be measured at small forward scattering angles, the beam divergence in the scattering plane must be minimized. This requirement is in conflict with the optical LaGrange invariant for a system with a 50 micron aperture. The conflict is avoided by use of an anamorphic lens system that produces a focus with a large aspect ratio in one dimension. The light projected from cylindrical lens 208 produces a light beam having a beam waist volume of 50×50×2000 microns. As can be seen in FIG. 5 (the vertical view of the system) the anamorphic lens system provides a low divergence in the scattering plane (parallel to the 2000 micron dimension and in the plane of FIG. 4) that increases the sampling volume and provides for a better statistical sampling of the particle samples in channel 11. The anamorphically modified incident light 217 enters the optical element 10 at sidewall 13 and travels through the optical element. The incident light 217 exits the optical element at channel wall 14 where it is focused onto particles 210 contained by the particle stream flowing in channel 11. The incident light 217 and the light scattered by the particles 210 enters the opposite channel wall 17 and travels again through an opposite side of the optical element, exiting sidewall 12.

As discussed above, due to the channel's width being proximate to the spacing between the particles to be measured, only a minimal amount of re-scattering occurs within the channel 11 before the scattered light enters channel wall 17. The light exiting sidewall 12 is projected onto a second cylindrical lens 215, which recollimates the anamorphically modified incident light received from the optical element 10. The collimated incident light 217 and the scattered light 216 from lens 215 are next projected onto a collector lens 220 and focused onto detector array 209. The detector array 209 outputs analog signals representing the total scattered light intercepted by individual detector elements of the detector array 209. The analog detector array output signals are converted to digital signals by A/D converter 211 and subsequently processed by a programmable computing device 212, using well known inversion techniques to obtain the desired particle size distribution.

Figure 6:
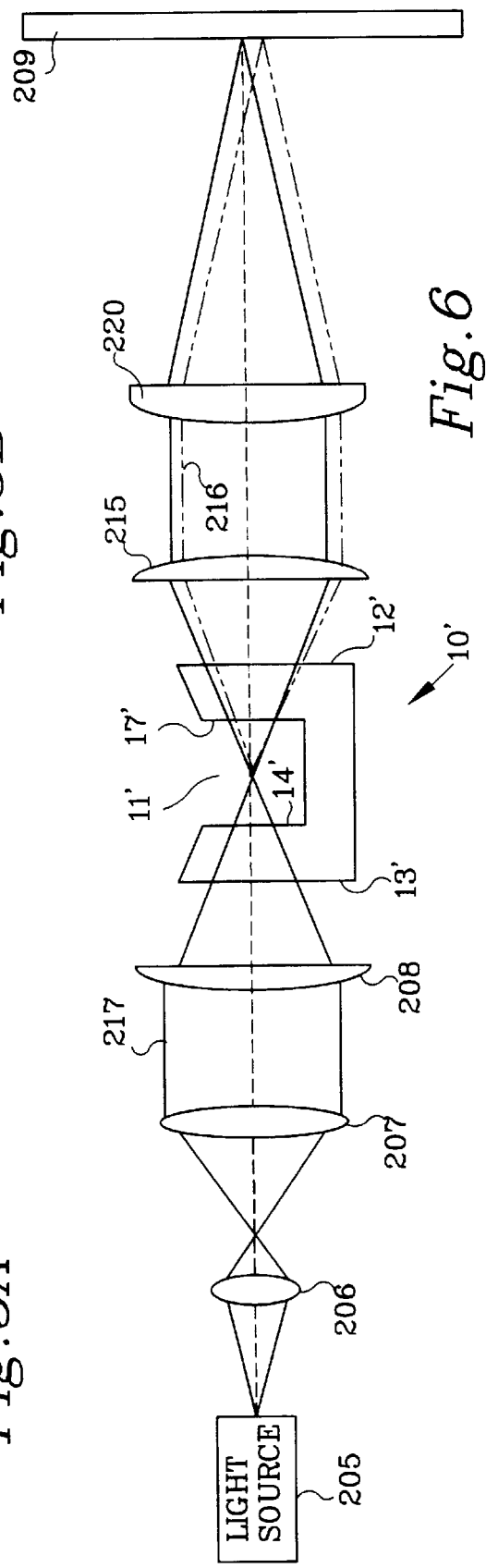
FIG. 6 depicts the system of the present invention in a vertical block diagram view, including the optical element of FIG. 3B.

The system of the present invention just described operates identically for an optical element having a 300 micron channel 11' shown in FIG. 6. It will be well understood by those skilled in the art that, depending on the size of particles to be analyzed, the proper optical element having a channel of an appropriate pathlength width and depth is used with the system of the present invention. However, in a system requiring a broad range of analysis, the sample cell can be configured to include both the smaller, for example, the 50 micron channel, and the larger, for example, the 300 micron channel, optical elements 10, 10'. Each optical element would be mounted in series with the stream flowing from one optical element to the next in the course of the process stream flow within the sample cell. A separate light source would be used for each optical element installed; however, a single light collection lens and detector could be used that would sequentially collect the incident and scattered light from each optical element by activating each source and recording each corresponding set of scattered light signals in sequence and, therefore, only one detector array and associated A/D converter and processing computer would be required to be used. In such a system, a means for measuring particle sizes between 0.1 and 3000 microns at high concentrations can be made by using the appropriately sized optical elements.

The present invention has been described with particular reference to the preferred embodiments thereof. It will be obvious that various changes and modifications can be made therein without departing from the spirit and scope of the invention as defined in the appended claims.

What is claimed is:

1. In an apparatus for determining the size distribution of small particles contained in a process stream, said apparatus including a sample cell having an inlet for receiving a sample portion of said process stream and an outlet for returning said sample portion to said process stream, a light source for generating light energy, a detector array for receiving light energy and means for translating the detected light energy into particle size distribution, a system for detecting the angular distribution of scattered light that results when said sample portion is irradiated by said light source comprising:

a) a light delivery arrangement that anamorphically modifies said light energy received from said light source and projects said anamorphically modified light energy to said sample cell;

b) an optical element contained in said sample cell, said optical element including a passage exposed to the sample portion of said process stream flowing in said sample cell, said passage sized to receive particles of a predetermined size range, and said anamorphically modified light energy is transmitted through said optical element and focused within said passage to irradiate the particle ensemble therein, said passage having a width equal to the optimal optical pathlength required to reduce multiple scattering of said anamorphically modified light energy focused on said particle ensemble in said passage, and a passage depth approximately equal to said passage width to allow exchange of particles between said process stream and said passage; and c) a light collection arrangement for collecting the light energy from said particle ensemble that is projected into said optical element, whereby said light collection arrangement collects the light energy escaping from said optical element and focuses the light energy collected onto said detector array.

2. The system as claimed in claim 1, wherein said optical element is generally rectangular in cross section and is composed of an optically clear material, said optical element further including:

a) planar first and second sidewalls extending, longitudinally between planar first and second end walls;

b) first and second top surfaces with each of said first and second top surfaces extending inwardly and obliquely from a top edge of a respective first and second sidewall toward the center of said optical element defining therebetween the periphery of a channel that extends parallel to said first and second sidewalls from said first end wall to said second end wall, whereby said channel comprises said optical element passage.

3. The system as claimed in claim 2, wherein said channel further includes first and second channel walls and said anamorphically modified light energy is projected at said optical element first sidewall and is internally transmitted through said optical element exiting said first channel wall, to be focused within said channel to irradiate the particle ensemble contained therein, and said light energy scattered by said particle ensemble enters said second channel wall and is transmitted through said optical element to exit said optical element at said second sidewall.

4. The system as claimed in claim 3 wherein said light delivery arrangement includes:

a) a projection lens that receives that light energy from said source of light energy and projects said light energy onto a collimator lens, said collimator lens producing a collimated beam of light parallel to an optical axis of the light energy emitted from said source of light energy; and b) an anamorphic projection device that receives and modifies said collimated beam of light into said anamorphically modified light energy, whereby said anamorphically modified light energy forms an anamorphic light beam that enters said optical element first sidewall and diverges into a focus in said channel in a vertical axis, with said anamorphic light beam extending substantially across said channel in a horizontal axis parallel to the optical axis of the light energy emitted from said source of light energy.

5. The system as claimed in claim 3 wherein said light collection arrangement includes:

a) an anamorphic collection lens that collects the light energy escaping said optical element second surface, said anamorphic collection lens modifying the scattered light energy and incident light energy collected into a collimated scatter beam and a collimated incident beam; and by a collector lens receiving said collimated scatter and incident beams, whereby said collector lens produces a divergent scatter beam and a divergent incident beam that is focused on said collector array.

6. The system as claimed in claim 5 wherein said anamorphic projection device is a first cylindrical lens and said collimated beam of light from said collimator lens is projected onto said first cylindrical lens, whereby it is modified by said first cylindrical lens and exits as said anamorphic light beam.

7. The system as claimed in claim 5 wherein said anamorphic collection device is a second cylindrical lens and said light energy escaping from said optical element second surface is projected on said second cylindrical lens, whereby it is modified by said second cylindrical lens and exits as said collimated scatter and said collimated incident beams.

8. An apparatus for determining the size distribution of small particles contained in a process stream, said apparatus including a sample cell having an inlet for receiving a sample portion of said process stream and an outlet for returning said sample portion to said process stream, a light source for generating light energy, a detector array for receiving light energy and means for translating the detected light energy into particle size distribution, a system for detecting the angular distribution of scattered light that results when said sample portion is irradiated by said light source comprising:

a) means for anamorphically modifying said light energy and projecting said anamorphically modified light energy to said sample cell;

b) means for permitting passage of particles of a predetermined size range of said process stream flowing in said sample cell, said anamorphically modified light energy substantially focused along said means for permitting passage to irradiate the particle ensemble therein, said passage means having a width equal to the optimal optical pathlength required to reduce multiple scattering of said anamorphically modified light energy focused on said particle ensemble in said passage means, and a passage depth approximately equal to said passage width to allow exchange of particles between said process stream and said passage means; and c) means for collecting the light energy scattered by said particle ensemble and for focusing the light energy scattered by said particle ensemble onto said detector array.

* * * * *

UNITED STATES PATENT AND TRADEMARK OFFICE
CERTIFICATE OF CORRECTION

PATENT NO. : 6,104,491
DATED : August 15, 2000
INVENTOR(S) : Michael N. Trainer

Page 1 of 1

It is certified that error appears in the above-identified patent and that said Letters Patent is hereby corrected as shown below:

<u>Claim 5, Column 8,</u>
Line 15, it reads "by collector lens" and it should read -- b) a collector lens --.

Signed and Sealed this

Eleventh Day of September, 2001

Attest:

*Attesting Officer*

NICHOLAS P. GODICI
*Acting Director of the United States Patent and Trademark Office*